United States Patent [19]

Osumi

[11] Patent Number: Plant 6,940

[45] Date of Patent: Jul. 25, 1989

[54] PEACH TREE, LADY LOU

[76] Inventor: Kengo Osumi, 15332 E. Adams, Parlier, Calif. 93648

[21] Appl. No.: 237,379

[22] Filed: Aug. 29, 1988

[51] Int. Cl.[4] ..... A01H 5/00
[52] U.S. Cl. ..... Plt./43
[58] Field of Search ..... Plt./43

*Primary Examiner*—Robert E. Bagwill
*Attorney, Agent, or Firm*—Worrel & Worrel

[57] ABSTRACT

A new and distinct variety of Peach Tree, denominated varietally as "Lady Lou" which is somewhat similar to the June Lady Peach Tree (U.S. Plant Pat. No. 3,022) with which it is most closely related but which is distinguished therefrom and characterized as to novelty by producing fruit which are mature for commercial harvesting approximately May 25 through June 5 in Fresno County, Calif., the subject variety maturing for commercial harvesting and shipment approximately ten days earlier than that of the June Lady Peach Tree.

1 Drawing Sheet

BACKGROUND OF THE NEW VARIETY

The present invention relates to a new and distinct variety of Peach Tree, hereinafter denominated varietally as "Lady Lou", and more particularly to a peach tree which is somewhat remotely similar in its physical characteristics to an unnamed peach tree to Chamberlin, Sr. (U.S. Plant Pat. No. 4,980) and to the June Lady Peach Tree (U.S. Plant Pat. No. 3,022), from which it was derived as a scaffold mutation, but from which it is distinguished therefrom and characterized principally as to novelty by producing fruit which have a uniform yellow colored flesh and which are mature for commercial harvesting and shipment approximately May 27 through June 4 in the San Joaquin Valley of central California.

ORIGIN AND ASEXUAL REPRODUCTION OF THE NEW VARIETY

The inventor has spent a substantial portion of his professional life engaged in farming operations. In this regard, the applicant, during routine orchard operations in late May, 1985, discovered a scaffold mutation of a June Lady Peach Tree (U.S. Plant Pat. No. 3,022) growing within the cultivated area of his commercial orchard which is located at 15332 East Adams in Parlier, Fresno County, Calif. The fruit produced by the scaffold mutation were noted at that time to have desirable characteristics and the inventor subsequently marked the scaffold mutation for future observation. To determine whether the traits of the newly discovered variety were true, the inventor, during the winter of 1985, removed bud wood from the aforementioned scaffold mutation and grafted it into test peach trees which were located on this same property. The inventor has continuously observed these test trees, and the original scaffold mutation and has evaluated the fruit produced therefrom, and it has subsequently been determined that the progeny produced from these test trees have the same identical characteristics as that produced by the original scaffold mutation.

SUMMARY OF THE NEW VARIETY

The Lady Lou Peach Tree hereof is characterized principally as to novelty by bearing fruit which have an attractive skin color and which further are ripe for commercial harvesting and shipment approximately May 27 through June 4 in the San Joaquin Valley of central California. The new variety Lady Lou matures approximately ten days earlier than the June Lady Peach Tree, (U.S. Plant Pat. No. 3,022) and at approximately the same time of the season as the unnamed Peach Tree to Chamberlin, Sr. (U.S. Plant Pat. No. 4,980). However, the new and novel variety, "Lady Lou" is biologically distinguishable from the Chamberlin, Sr. Peach Tree (U.S. Plant Pat. No. 4,980) by being derived from a scaffold mutation of a June Lady Peach Tree as contrasted with the unnamed peach tree to Chamberlin, Sr. (U.S. Plant Pat. No. 4,980) which was discovered as a newly found seedling of the June Lady Peach Tree (U.S. Plant Pat. No. 3,022).

BRIEF DESCRIPTION OF THE DRAWINGS

The accompanying drawing is a color photograph of three mature fruit, one of which has been divided in the axial plane to show the flesh and pit characteristics, together with a twig bearing representative leaves which display the coloration of the top and bottom surfaces thereof, and a representative stone, all of the subject variety.

DETAILED DESCRIPTION

Referring more specifically to the pomological details of this new and distinct variety of peach tree, the following has been observed under the ecological conditions prevailing at the applicant's orchard which is located at 15332 East Adams in Parlier, Calif. All major color code designations are by reference to the Dictionary of Color, by Maerz and Paul, Second Edition, 1950. Common color names are also employed occasionally.

TREE

Size:
*Generally.*—Average.
Form:
*Generally.*—Spreading. The final form of the tree is determined by pruning practices.
Productivity: Productive.
Regularity of Bearing: Regular.
Trunk:
*Diameter.*—Medium.
*Texture.*—Average.

*Color.*—Grayish-brown, the trunk color is not particularly distinctive of the subject variety.

Branches:

*Size.*—Medium.

*Surface texture.*—Average.

*Color.*—Brown, (15-C-7).

Lenticels:

*Numbers.*—Numerous.

*Average width.*—Approximately 1–2 mm.

*Average length.*—Approximately 5–7 mm.

LEAVES

Size:

*Generally.*—Medium to large.

Average length: Approximately 170–185 mm.

Average width: Approximately 40–42 mm.

Leaf form:

*Generally.*—Lanceolate.

Color

*Upper surface.*—Dark green, (24-J-9).

*Lower surface.*—Pale green, (21-J-9).

Marginal form:

*Generally.*—Finely serrate.

Glandular characteristics:

*Numbers.*—Variable. As a general matter, one to three glands may be evident.

Leaf petiole

*Average length.*—Approximately 10–11 mm.

*Average thickness.*—Approximately 2 mm.

Stem glands

*Numbers.*—Variable, one to three stem glands may be found.

*Arrangement.*—Alternate.

*Size.*—Small.

*Form.*—Reniform.

*Color.*—Green. The stem gland color of the subject variety is not particularly distinctive.

Stipules: No stipules are evident.

FLOWER BUDS

Generally: The overall size and appearance of the flower buds is considered average for this particular cultivar.

Form: Plump.

Pubescence: Yes, and free.

FLOWERS

Date of Bloom: Early March in the San Joaquin Valley of central California. This is considered early as compared with other peach cultivars.

Size: Variable, small to average.

Color:

*Generally.*—Light pink, although a salmon tinge may be evident on some of the flowers.

Pollen production: Abundant.

FRUIT

Maturity when described: Ripe for commercial harvesting and shipment approximately May 27 through June 4 in the San Joaquin Valley of central California.

Size:

*Generally.*—Uniform.

Average diameter in the axial plane: Approximately 66–70 mm.

Average diameter transverse in the suture plane: Approximately 66–71 mm.

Average diameter transverse at right angles to the suture plane: Approximately 67–69 mm.

Form:

*Uniformity.*—Uniform.

Symmetry: Symmetrical.

Suture:

*Generally.*—The suture appears as an inconspicuous line which extends from the base to the pistil point. Further a deep depression appears near the base.

*Average length.*—Approximately 90–95 mm.

Ventral surface:

*Shape.*—Rounded.

Stem cavity:

*Shape.*—Rounded.

*Average length.*—Approximately 25–30 mm.

*Average Width.*—Approximately 15–20 mm.

*Depth.*—Approximately 10 mm.

Base:

*Shape.*—Rounded.

Apex:

*Form.*—Rounded.

Pistil point:

*Position.*—Variable, appearing alternatively in the apical or oblique positions.

Stem

*Average length.*—Approximately 10–11 mm.

*Average thickness.*—Approximately 4 mm.

*Thickness.*—Average.

Skin:

*Texture.*—Medium.

Tendency to crack: Not observed.

Ground color: Light yellow, (5-I-6).

Blush color: Red, (10-L-6).

Pubescence: Present, however it is considered slight.

Flesh color: Approximately the same color as the ground color, that is a light yellow, (5-I-6).

Surface of the pit cavity:

*Color.*—Approximately the same as the ground color, (5-I-6).

Amygdalin: Present but scant.

Juice Production: Juicy.

Flavor: Generally considered subacid.

Aroma: Distinct.

Texture: Average.

Fibers: Present and characterized as being fine.

Ripening:

*Generally.*—Even.

Eating quality: Considered good as compared with other varieties which ripen in approximately the same season.

STONE

Attachment: The subject variety is considered semi-freestone by nature.

Fibers:

*Generally.*—Considered long. Further, the fibers adhere to the pit at the base thereof.

Average length: Approximately 31–37 mm.

Average width: Approximately 23–25 mm.

Average thickness: Approximately 18–19 mm.

Form: Oval and beaked.

Dorsal edge:

*Generally.*—A deep groove appears over the entire length of the stone.

Ventral edge:

*Generally.*—Thin and having a wing throughout.

Base:

*Form.*—Straight.

Sides: Equal. Further, pits may be observed near the base, and grooves may appear near the apex.

Grooves:

*Form.*—These appear rounded and are located near the base.

Color: Light brown, this color is not particularly distinctive.

Tendency to split: Not observed.

Fruit use: Fresh market and dessert peach for both local and long distance shipping.

Keeping quality: Good.

Shipping quality: Good.

Resistance to disease: No particular susceptibilities are noted.

Although the new variety of peach tree possesses the described characteristics as a result of the growing conditions prevailing in the San Joaquin Valley of central California, it is to be understood tht variations of the usual magnitude and characteristics incident to growing conditions, fertilization, pruning and pest control are to be expected.

Having thus described and illustrated my new variety of peach tree, what I claim is:

1. A new and distinct variety of peach tree to be denominated varietally as "Lady Lou" substantially as illustrated and described and which is characterized principally as to novelty by its production of fruit which are somewhat similar in their overall appearance to the fruit produced by the June Lady Peach Tree, (U.S. Plant Pat. No. 3,022) from which it was derived as a chance scaffold mutation but which is distinguished therefrom by producing fruit which are ripe for commercial harvesting and shipment approximately ten days earlier than the fruit produced by the June Lady Peach Tree.

* * * * *

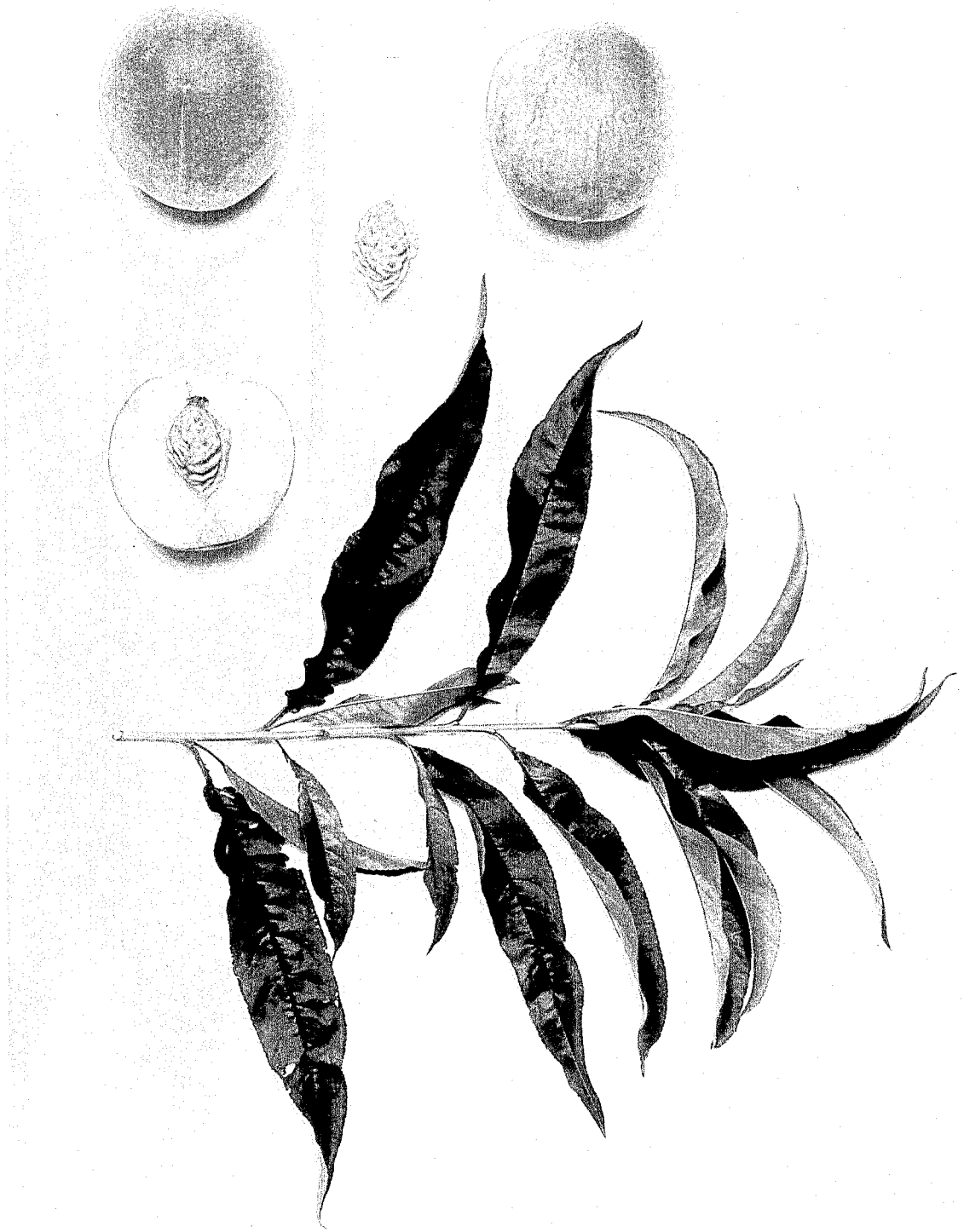

UNITED STATES PATENT AND TRADEMARK OFFICE

CERTIFICATE OF CORRECTION

PATENT NO. : PP 6,940

DATED : July 25, 1989

INVENTOR(S) : Kengo Osumi

It is certified that error appears in the above-identified patent and that said Letters Patent is hereby corrected as shown below:

Column 4, line 24, after "Stem" on line 27 delete "Thickness.--Average."

Column 4, line 28, after "Skin" insert the following line --Thickness - Average.--.

Signed and Sealed this

Tenth Day of July, 1990

*Attest:*

HARRY F. MANBECK, JR.

*Attesting Officer*

*Commissioner of Patents and Trademarks*